(12) United States Patent
Fortuna et al.

(10) Patent No.: US 12,251,246 B2
(45) Date of Patent: Mar. 18, 2025

(54) RADIOLOGICAL IMAGING DEVICE WITH IMPROVED FUNCTIONALITY

(71) Applicant: Epica International, Inc., San Clemente, CA (US)

(72) Inventors: Damiano Fortuna, Rignano sull'Arno (IT); Leonardo Manetti, Montevarchi (IT); Massimiliano Leonori, Lucca (IT)

(73) Assignee: EPICA INTERNATIONAL, INC., San Clemente, CA (US)

( * ) Notice: Subject to any disclaimer, the term of this patent is extended or adjusted under 35 U.S.C. 154(b) by 490 days.

(21) Appl. No.: 17/505,619

(22) Filed: Oct. 19, 2021

(65) Prior Publication Data

US 2022/0117568 A1   Apr. 21, 2022

(30) Foreign Application Priority Data

| Oct. 19, 2020 | (IT) | 102020000024583 |
| Oct. 19, 2020 | (IT) | 102020000024592 |
| Oct. 19, 2020 | (IT) | 102020000024598 |
| Oct. 19, 2020 | (IT) | 102020000024601 |
| Oct. 19, 2020 | (IT) | 102020000024607 |
| Oct. 19, 2020 | (IT) | 102020000024613 |
| Oct. 18, 2021 | (WO) | PCT/IB2021/059550 |

(51) Int. Cl.
*A61B 6/03* (2006.01)
*A61B 6/00* (2006.01)
(Continued)

(52) U.S. Cl.
CPC ............ *A61B 6/032* (2013.01); *A61B 6/035* (2013.01); *A61B 6/08* (2013.01); *A61B 6/4007* (2013.01); *A61B 6/4405* (2013.01); *A61B 6/4476* (2013.01); *A61B 6/5247* (2013.01); *A61B 6/56* (2013.01); *A61B 34/10* (2016.02); *A61B 90/13* (2016.02); *A61B 90/361* (2016.02);
(Continued)

(58) Field of Classification Search
None
See application file for complete search history.

(56) References Cited

U.S. PATENT DOCUMENTS 8,102,963 B2 * 1/2012 Shapiro .................. A61B 6/032
378/8
8,888,364 B2 * 11/2014 Bailey ..................... A61B 6/508
378/198

(Continued)

FOREIGN PATENT DOCUMENTS

| DE | 102005024157 A1 | 11/2006 |
| DE | 102014207568 A1 | 10/2015 |
| WO | 2016/168671 A1 | 10/2016 |

OTHER PUBLICATIONS

Iadanza et al. "FMECA Design Analysis: Risk Management for the Manufacture of a CBCT Scanner," IEEE Access, vol. 7, Dec. 2019, pp. 181546-181564.

(Continued)

*Primary Examiner* — Thomas R Artman
(74) *Attorney, Agent, or Firm* — STEPTOE LLP; Carl B. Wischhusen

(57) ABSTRACT

A radiological imaging device comprises a source defining an acquisition axis, a detector, a power supply, a control unit to control at least the source and the detector, and a connector for an additional source to the power supply and the control unit.

4 Claims, 6 Drawing Sheets

(51) Int. Cl.
*A61B 6/08* (2006.01)
*A61B 6/40* (2024.01)
*A61B 34/10* (2016.01)
*A61B 90/00* (2016.01)
*A61B 90/13* (2016.01)
*A61B 34/20* (2016.01)

(52) U.S. Cl.
CPC ....... *A61B 6/4435* (2013.01); *A61B 2034/107* (2016.02); *A61B 2560/0437* (2013.01)

(56) References Cited

U.S. PATENT DOCUMENTS

| | | | |
|---|---|---|---|
| 9,510,793 B2* | 12/2016 | Stoutenburgh | A61B 6/4233 |
| 9,526,461 B2* | 12/2016 | Gregerson | A61B 6/4014 |
| 10,265,042 B2* | 4/2019 | Stoutenburgh | A61B 6/4233 |
| 10,413,265 B2* | 9/2019 | Stoutenburgh | A61B 6/032 |
| 10,772,577 B2* | 9/2020 | Fortuna | A61B 34/30 |
| 10,835,190 B2* | 11/2020 | Gregerson | A61B 6/4405 |
| 10,959,783 B2* | 3/2021 | Gregerson | A61B 5/0036 |
| 10,973,484 B2* | 4/2021 | Stoutenburgh | A61B 6/487 |
| 11,510,635 B2* | 11/2022 | Fortuna | A61B 6/4405 |
| 11,540,786 B2* | 1/2023 | Stoutenburgh | A61B 6/487 |
| 11,857,269 B2* | 1/2024 | Gregerson | A61B 5/055 |
| 2009/0252285 A1 | 10/2009 | Shapiro et al. | |
| 2012/0140899 A1 | 6/2012 | Bailey et al. | |
| 2013/0343509 A1 | 12/2013 | Gregerson et al. | |
| 2014/0107473 A1* | 4/2014 | Dumoulin | A61B 17/1703 606/130 |
| 2014/0275953 A1 | 9/2014 | Gregerson et al. | |
| 2015/0208993 A1 | 7/2015 | Stoutenburgh et al. | |
| 2015/0208998 A1* | 7/2015 | Stoutenburgh | A61B 6/032 378/11 |
| 2016/0302871 A1* | 10/2016 | Gregerson | A61B 90/39 |
| 2017/0079606 A1* | 3/2017 | Stoutenburgh | A61B 6/0407 |
| 2017/0354387 A1* | 12/2017 | McCarthy | A61B 34/20 |
| 2019/0038240 A1 | 2/2019 | Fortuna et al. | |
| 2019/0192097 A1* | 6/2019 | Stoutenburgh | A61B 6/06 |
| 2020/0305825 A1* | 10/2020 | Stoutenburgh | A61B 6/487 |
| 2021/0000432 A1* | 1/2021 | Fortuna | A61B 6/4405 |
| 2021/0022691 A1* | 1/2021 | Gregerson | A61B 6/4405 |
| 2021/0052241 A9* | 2/2021 | Stoutenburgh | A61B 6/4233 |
| 2021/0106391 A1* | 4/2021 | Gregerson | A61B 5/0036 |
| 2022/0117568 A1* | 4/2022 | Fortuna | A61B 6/4007 |

OTHER PUBLICATIONS

Rapporto Di Ricerca and Opinione Scritta (Search Report and Written Opinion) from IT Application No. 202000024583, Jun. 21, 2021, 8 pages.

Rapporto Di Ricerca and Opinione Scritta (Search Report and Written Opinion) from IT Application No. 202000024592, Jun. 22, 2021, 8 pages.

Rapporto Di Ricerca and Opinione Scritta (Search Report and Written Opinion) from IT Application No. 202000024598, Jun. 23, 2021, 8 pages.

Rapporto Di Ricerca and Opinione Scritta (Search Report and Written Opinion) from IT Application No. 202000024601, Jun. 23, 2021, 8 pages.

Rapporto Di Ricerca and Opinione Scritta (Search Report and Written Opinion) from IT Application No. 202000024607, Jul. 8, 2021, 9 pages.

Rapporto Di Ricerca and Opinione Scritta (Search Report and Written Opinion) from IT Application No. 202000024613, Jul. 8, 2021, 10 pages.

* cited by examiner

RADIOLOGICAL IMAGING DEVICE WITH IMPROVED FUNCTIONALITY

CROSS-REFERENCE TO RELATED APPLICATIONS

This application is based on and claims priority from the following applications: Italian Patent App. Nos. 102020000024583, 102020000024592, 102020000024598, 102020000024601, 102020000024607, 102020000024613, all filed Oct. 19, 2020, and International Application No. PCT/IB2021/059550, filed Oct. 18, 2021, each of which is incorporated herein by reference in its entirety.

BACKGROUND

The present invention relates to a radiological imaging device with improved functionality of the type specified in the preamble of the first claim. In particular, the invention relates to a device configured to be used in the medical/veterinary field to at least obtain radiological images (such as tomography) of at least a portion of the internal anatomy of a patient.

Known radiological imaging devices, regardless of the analysis performed (tomography, radiology, or fluoroscopy) have the same basic structure. This basic structure provides a bed on which the patient is arranged, a control station for the device; an O or C-shaped gantry, defining a cavity wherein the portion to be analyzed and carrying out the radiological acquisition is inserted; and a support supporting the gantry and the bed and able to translate the bed and gantry between them. The gantry provides an X-ray source; a detector that receives x-rays after they have passed through the bed and the patient.

In the cases of a radiological device for CAT (Computed Axial Tomography) or CT (Computed Tomography), there is a rotation organ that rotates the source and detector around the patient allowing the device to acquire images at different angles and therefore to generate a three-dimensional reconstruction of the patient. Examples of these devices are reported in US2004125915A1, WO2014001834 and US20030072416.

The known art described includes some important drawbacks. In particular, known radiological imaging devices are particularly bulky and therefore of reduced portability. Another drawback is that the radiological imaging devices currently in use require slow and inaccurate aiming. In fact, the aiming is performed manually by the operator who, using a camera close to the source, must understand when the source is centered with respect to the portion to be analyzed. An important drawback is also represented by the fact that the known radiological imaging devices allow the execution of a limited type of acquisitions by requiring the purchase of several machines, each of which is specific for a type of radiological imaging. Another drawback is represented by the fact that the known radiological imaging devices are made up of numerous and complex apparatuses that make the devices particularly expensive (both in the purchase phase and in the maintenance phase) and above all difficult to manufacture and use.

In this situation, the technical task underlying the present invention is to devise a radiological imaging device capable of substantially obviating at least part of the aforementioned drawbacks. Within the scope of this technical task, an important object of the invention is to obtain a radiological imaging device of reduced size and easy to transport. Another object of the invention is to provide a radiological imaging device that is easy to use and that, in particular, allows precise and rapid centering with respect to the portion to be analyzed that allows the execution of several types of acquisitions. Another object of the invention is to have an imaging device that is low cost and above all is easy to manufacture and use.

The technical task and the specified aims are achieved by a radiological imaging device as described in the detailed description that follows.

BRIEF DESCRIPTION OF THE DRAWINGS

The characteristics and advantages of the invention are clarified below by the detailed description of preferred embodiments of the invention, with reference to the accompanying figures, in which.

DETAILED DESCRIPTION

Figure 1:
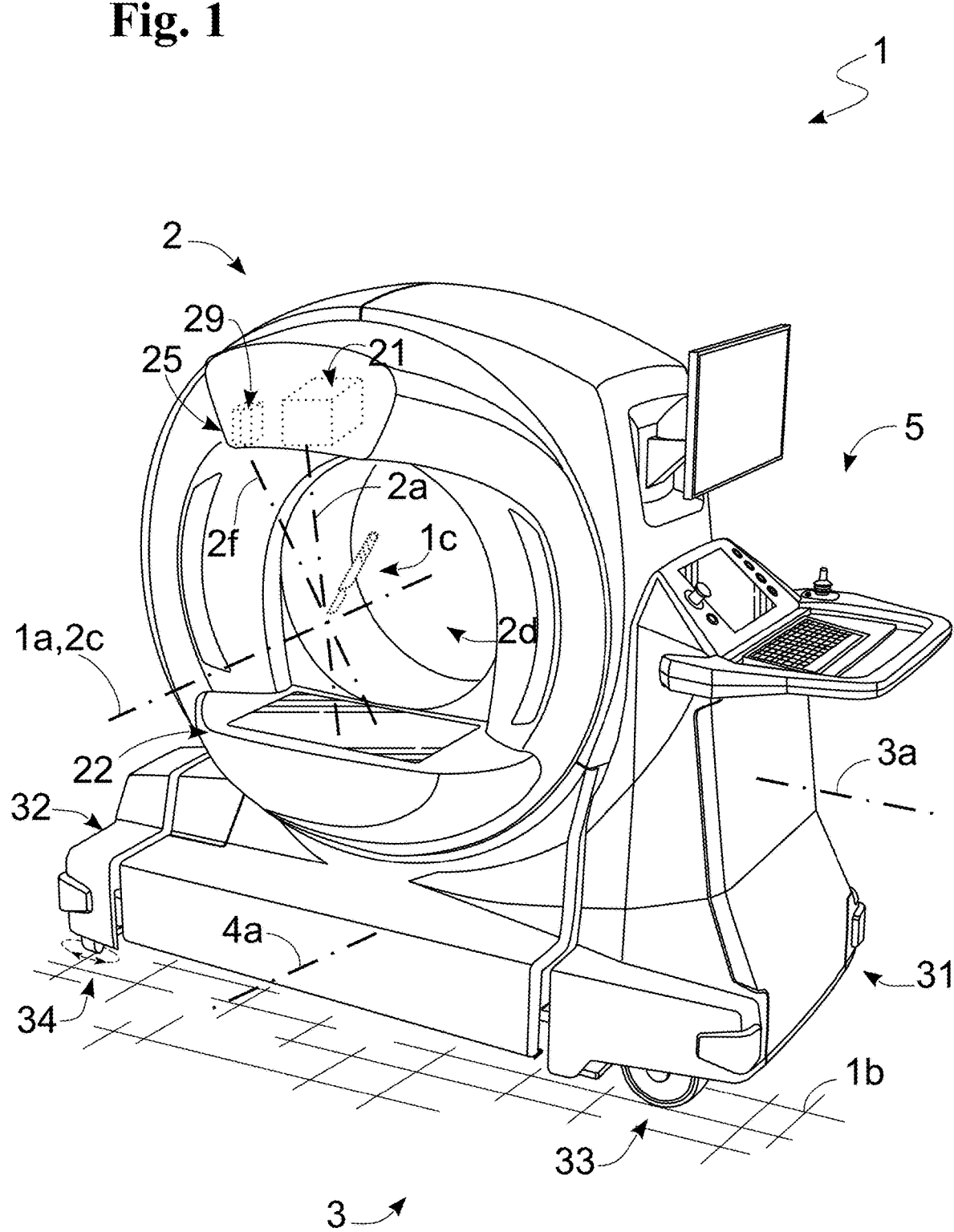
FIG. 1 shows, in scale, a radiological imaging device according to the invention.
Figure 2:
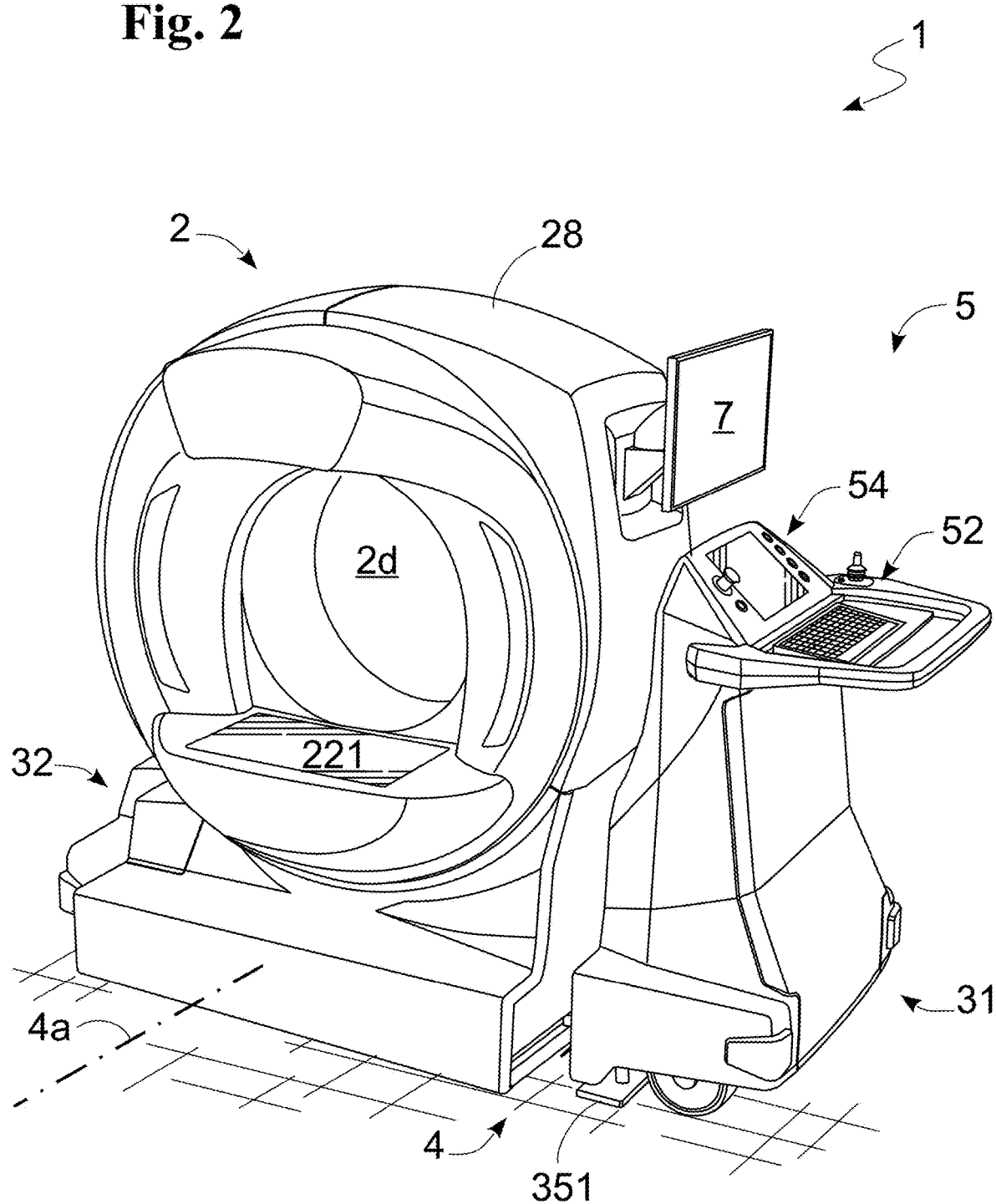
FIG. 2 illustrates, in scale, the device of FIG. 1 in a different position.
Figure 3:
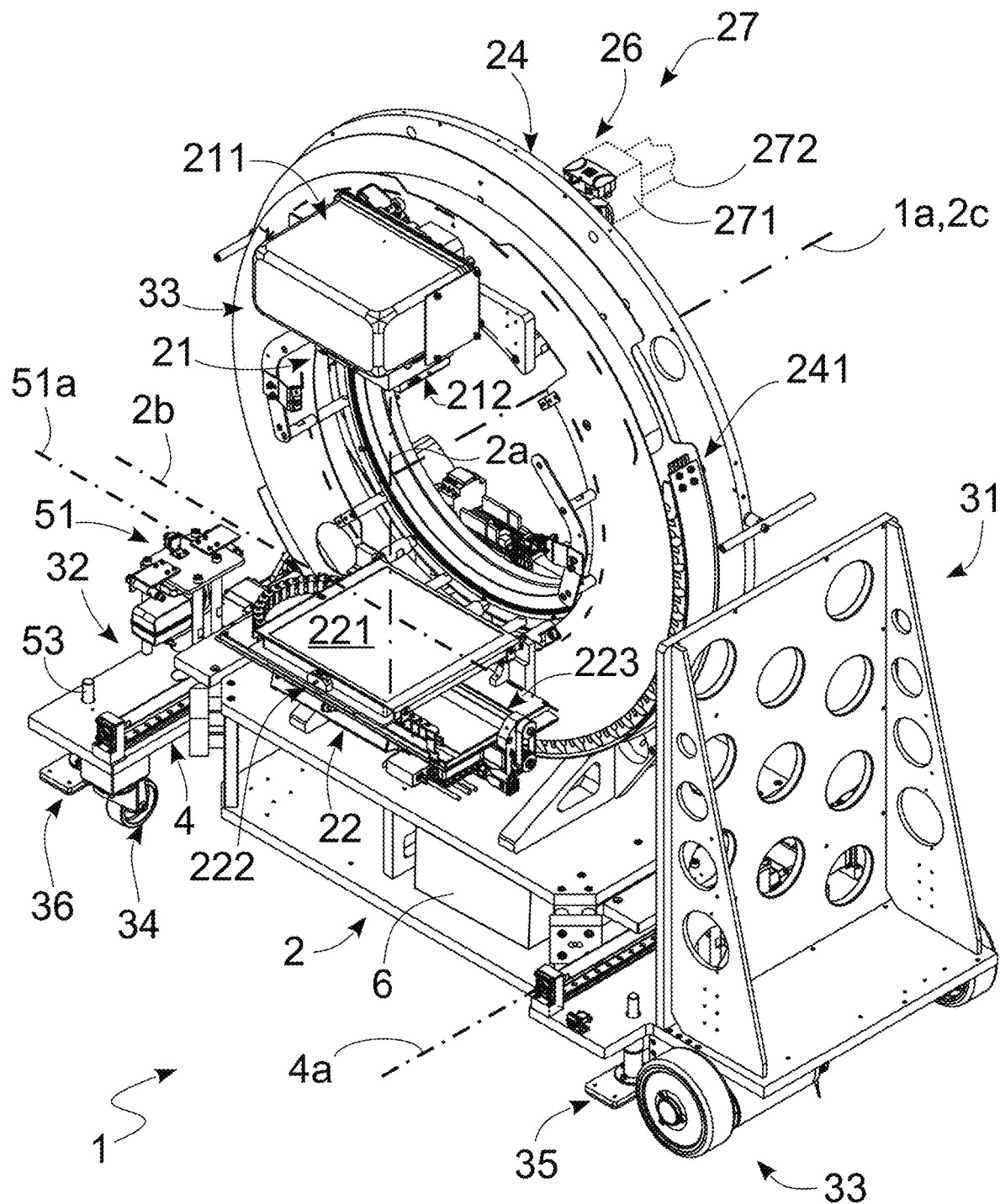
FIG. 3 shows, in scale, of an assembly of the radiological imaging device according to the invention.

In the present document, the measurements, values, shapes, and geometric references (such as perpendicularity and parallelism), when associated with words like "about" or other similar terms such as "approximately" or "substantially," are to be considered as except for measurement errors or inaccuracies due to production and/or manufacturing errors, and, above all, except for a slight divergence from the value, measurements, shape, or geometric reference with which it is associated. For instance, these terms, if associated with a value, preferably indicate a divergence of not more than 10% of the value. Moreover, when used, terms such as "first," "second," "higher," "lower," "main," and "secondary" do not necessarily identify an order, a priority of relationship, or a relative position, but can simply be used to clearly distinguish between their different components. The measurements and data reported in this text are to be considered, unless otherwise indicated, as performed in the International Standard Atmosphere ICAO (ISO 2533).

Unless otherwise specified, as results in the following discussions, terms such as "treatment," "computing," "determination," "calculation," or similar, refer to the action and/or processes of a computer or similar electronic calculation device that manipulates and/or transforms data represented as physical, such as electronic quantities of registers of a computer system and/or memories in, other data similarly represented as physical quantities within computer systems, registers or other storage, transmission or information displaying devices.

With reference to the Figures, the radiological imaging device according to the invention is globally indicated with the number 1. It is configured to be used both in the medical and veterinary fields for the production and/or interpretation for diagnostic and/or therapeutic purposes of a radiological image (radiological imaging) of at least a portion of a patient to be analyzed. In particular, device 1 is configured to perform at least one tomography with suitably multiple stacks (or rather radiological (preferably tomographic) acquisitions of portions of the patient as described below). It should be noted that the patient, during the acquisition, is on a radiological support (such as a radiological bed) defining a support surface for the patient and in particular for the portion to be analyzed.

The radiological image is a representation of at least a portion to be analyzed inside the patient. The radiological image can include a sector of interest representative of the portion to be analyzed suitably internal, optionally a perimeter sector of the sector of interest (for example identifiable in the patient's skin) and preferably a sector of non-interest that is not representative of the patient and visually separated from the sector of interest due to the perimeter sector. In the case of 2D images, the sector of interest and that of non-interest can be surfaces/areas, while the perimeter sector can be represented by a line; while in the case of 3D images the sector of interest and that of non-interest can be volumes, while the perimeter sector can be represented by a surface.

Radiological imaging device 1 may comprise a radiological support. The radiological support is known per se. In addition, the radiological image may comprise and preferably defines an intervention target and an intervention trajectory.

Radiological imaging device 1 is configured to rest on a support surface 1b such as a walkable plane of a health facility. Conveniently it can be moved along said support surface 1b. Radiological imaging device 1 can define a longitudinal axis 1a suitably substantially not perpendicular and in detail substantially parallel to support surface 1b when radiological imaging device 1 is in use (hereinafter simply "in use"), or rather resting on said support surface 1b.

In this document, terms such as "vertical" and "horizontal" define an axis, a displacement or other, respectively, substantially perpendicular or substantially parallel to support surface 1b when radiological imaging device 1 is in use.

Radiological imaging device 1 can comprise a unit for controlling the operation of the device itself. The control unit is configured to control and/or actuate, automatically and/or in response to a command given by the operator, device 1 and in particular at least part of and preferably at least one acquisition procedure or method 100 of radiological imaging carried out using radiological imaging device 1 and described below. Acquisition procedure 100 comprises the use of radiological imaging device 1. Radiological imaging device 1 can comprise a gantry 2 configured to perform the radiological acquisition of at least a portion to be analyzed. Gantry 2 can define a prevalent development axis substantially parallel to longitudinal axis 1a. It can define a front face, a back face, and one or more side faces (in some cases two). The front face and a back face are substantially perpendicular to the prevalent development axis and then to longitudinal axis 1a. Gantry 2 can be C-shaped (called a "C-arm") or is preferably O-shaped ("O-ring").

Gantry 2 can define a scanning zone 2d wherein at least the portion to be analyzed is available. The front and rear faces can be on opposite sides respect to scanning zone 2d. In detail, they can define the bases of the volume defining scanning zone 2d.

Gantry 2 can define a front face, a back face, and two side faces. In use, the faces are substantially transverse and in detail substantially perpendicular to support surface 1b. The faces can identify the four lateral faces of an inscription cuboid of gantry 2. The rear and front faces can be substantially transverse and in detail substantially perpendicular to longitudinal axis 1a. The lateral faces can be substantially parallel to longitudinal axis 1a.

Gantry 2 can comprise a source 21 (schematically shown in FIG. 1) configured to emit and then define an acquisition beam and an acquisition axis 2a. Source 21 is in data connection with and therefore can be controlled by the control unit. In use, acquisition axis 2a can be substantially transverse to support surface 1b. Source 21 can emit an X-ray acquisition beam. Source 21 can comprise an emitting body 211 of said acquisition beam defining acquisition axis 2a; a collimator 212 configured to vary the section (in detail, the extension and/or the profile) of the acquisition beam; and in some cases, a light source configured to illuminate scanning zone 2d and in particular the portion to be analyzed, favoring the correct positioning of the acquisition beam.

Advantageously, source 21 can be without a light source, as described in detail below. It can be placed in correspondence with the front face of gantry 2. Source 21 can comprise a pointing apparatus configured to project a figure through which to perform the centering and therefore the pointing of the source with respect to scanning zone 2d and in particular to the portion to be to analyzed.

Gantry 2 can comprise a detector 22 configured to have the acquisition beam incident thereupon after the acquisition beam has crossed the portion to be analysed. Detector 22 can be configured to obtain at least one radiological acquisition when said beam is incident thereupon. Said at least one radiological acquisition is then used by the control unit, in a known way, to obtain at least a radiological image. Detector 22 defines a surface sensitive to the acquisition beam. It is in data connection with and therefore can be controlled by the control unit. The sensitive surface can be substantially perpendicular to acquisition axis 2a. Detector 22 can comprise a sensitive element 221 defining the sensitive surface. Detector 22 can be placed to correspond to the front face of gantry 2. Detector 22 can comprise a projector 222 configured to project an optical marker in scanning zone 2d, or rather on the support surface and in particular on the portion to be analysed so as to allow a precise positioning of detector 22 and therefore of source 21. The optical marker can be a cross. Projector 222 can comprise at least one light source (for example a laser source) defining said optical marker. In detail, it comprises two light sources suitably configured to emit two mutually incident optical emissions, defining said optical cross marker. Projector 222 can be proximal to the sensitive surface. It can be integral with sensitive element 221.

Detector 22 can comprise a waving device 223 configured to translate at least sensitive element 221 along a waving axis 2b. Waving axis 2b can be substantially perpendicular to acquisition axis 2a. Waving axis 2b can be substantially parallel to the sensitive surface.

Gantry 2 can comprise a support for source 21 and detector 22. The support and therefore gantry 2 can comprise a rotor 23 supporting at least source 21 and detector 22; and a stator 24 supporting rotor 23 and configured to rotate rotor 23 (and therefore the components constrained thereto) suitably defining a rotation axis 2c and preferably controlled by the control unit. Rotation axis 2c can be substantially parallel to longitudinal axis 1a. The back and front faces of gantry 2 can be perpendicular to axis of rotation 2c. The one or more lateral faces of gantry 2 can be parallel to axis of rotation 2c.

Gantry 2, as above described, and preferably rotor 23 can define scanning zone 2*d*. Source 21 and detector 22 can be integral with rotor 23. They can be on the opposite side with respect to scanning zone 2*d*. Preferably, stator 24 is configured to rotate rotor 23 while keeping acquisition axis 2*a* resting on a resting plane which, in use, can be practically transverse and in detail almost perpendicular to support surface 1*b*. Stator 24 comprises a rotation member 241 for the rotation of rotor 23. As stated above, rotation axis 2*c* can be substantially parallel to longitudinal axis 1*a*. In use, rotation axis 2*c* can be substantially non-perpendicular and in detail substantially parallel to support surface 1*b*. Rotation member 241 can be of a known type. Rotation member 241 may comprise a rotation encoder configured to measure rotation about rotation axis 2*c*. It should be noted that the control unit can be at least in part and in detail totally constrained to stator 24.

Gantry 2 can comprise an optical pointer 25 (schematically shown in FIG. 1) integral with rotor 23 and configured to project an optical reference 2*e* in scanning zone 2*d*, or rather on the support surface and in particular on the portion to be analyzed. Optical reference 2*e* can be a cross. Optical pointer 25 is in data connection with and therefore can be controlled by the control unit. Optical pointer 25 is configured to project optical reference 2*e* by defining a pointing axis 2*f*. Pointing axis 2*f* can be inclined with respect to the acquisition axis, suitably defining, with respect to rotation axis 2*c*, a spreading angle therefore having a vertex on said rotation axis 2*c*. The spreading angle can be substantially less than 180°, in detail at 90°, more in detail at 60° and more in detail still at 45°. It is preferably substantially comprised between 5° and 45° and more precisely between 10° and 30°. Pointing 2*f* and acquisition 2*a* axes can be substantially coplanar and in detail resting on said resting plane. They can be substantially incident rotation axis 2*c* suitably in the same point.

Optical pointer 25 can comprise at least one emitter (suitably laser) defining said optical reference 2*e*. In detail, it comprises two emitters suitably configured to emit two mutually incident optical beams defining said cross-shaped optical reference 2*e*. Optical pointer 25 can be angularly spaced from detector 22 with respect to rotation axis 2*c* by an angle at least equal to 120° and in detail substantially comprised between 130° and 160°. Consequently, the operator can check the correct positioning of source 21 and detector 22 with respect to scanning zone 2*d* and in particular to the portion to be analyzed by using alternatively projector 223 or optical pointer 25.

Figure 4:
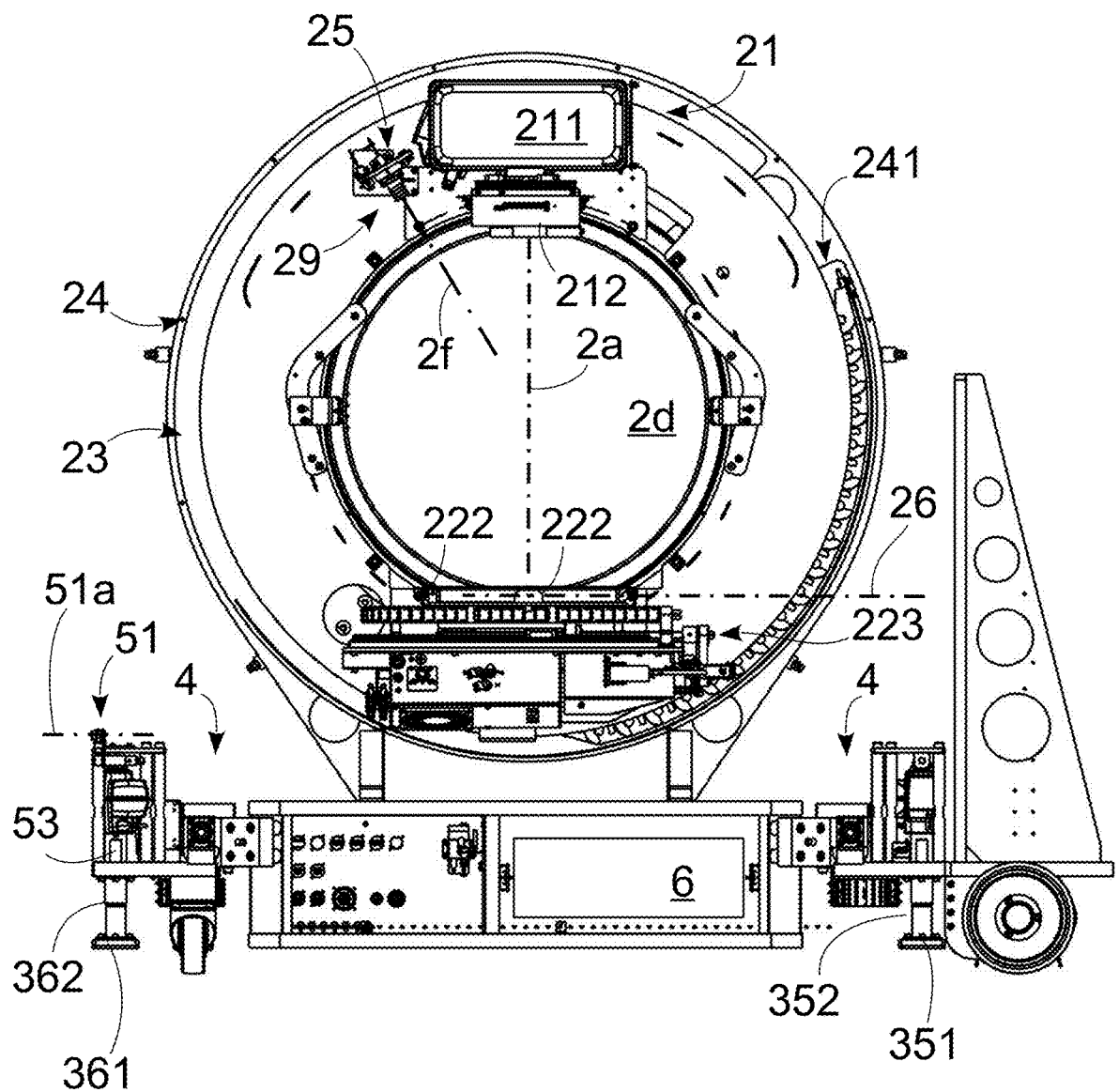
FIG. 4 depicts, in scale, a second view of the assembly of FIG. 3.

Gantry 2 can comprise a connector 26 for an additional source 27. Connector 26 is configured to allow additional source 27 to be associated with radiological imaging device 1 which, therefore, is equipped with sources 21 and 27. Connector 26 is in data connection with the control unit, which can therefore be placed in data connection with additional source 27 and, for example, command its operation. It is a quick fit type connector. Connector 26 is of the resolvable type so as to allow to constrain or separate additional source 27 from gantry 2. Connector 26 can be constrained on the opposite side with respect to source 21 and detector 22 (FIG. 4) and in detail in correspondence with the rear face of gantry 2. Connector 26 can be integral with the support and in detail with stator 24 or alternatively with rotor 23.

Figure 5:
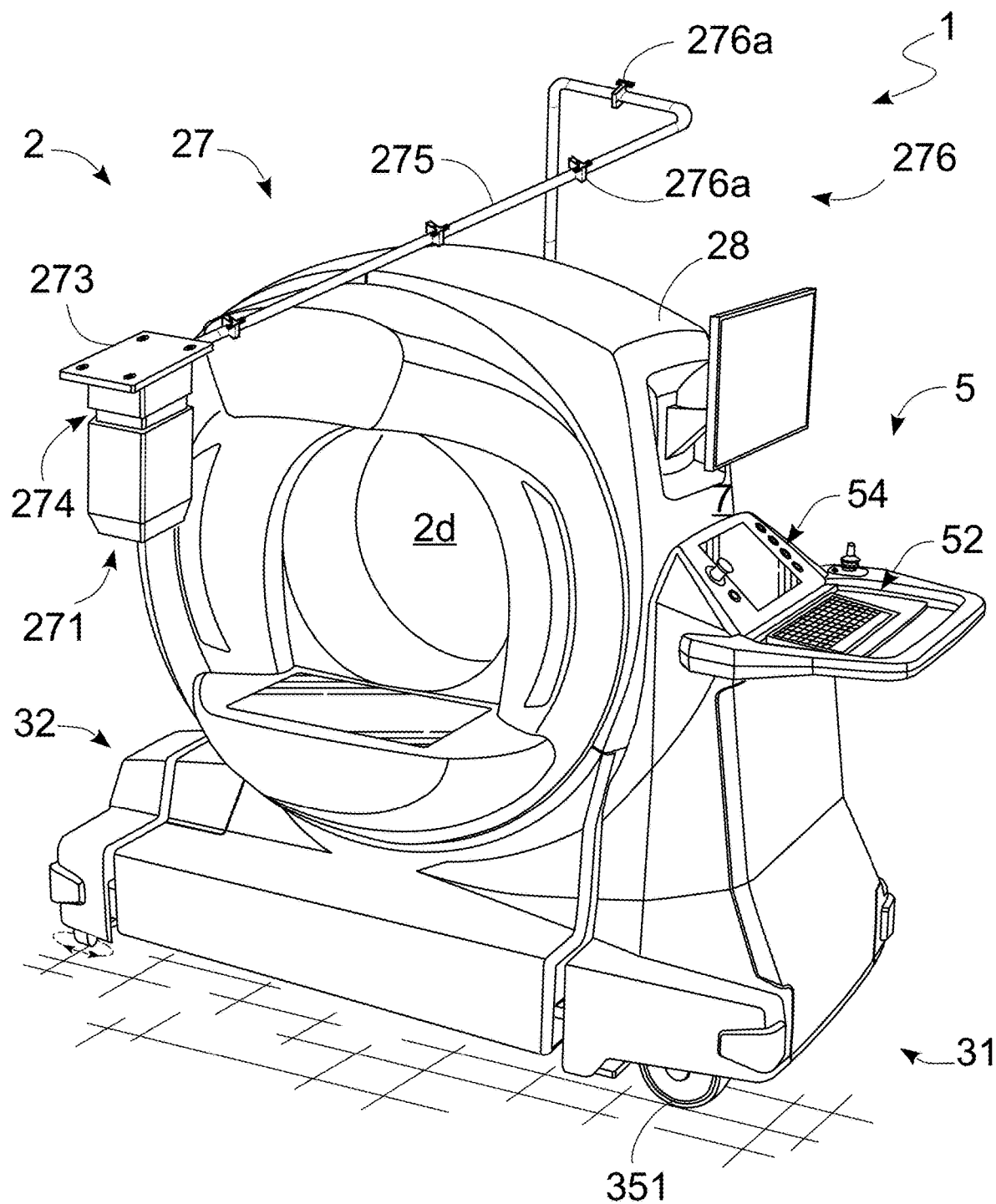
FIG. 5 shows, in scale, another radiological imaging device according to the invention.

Gantry 2 can comprise additional source 27 (FIG. 5). Additional source 27 can be of the same type as source 21. Alternatively, it can be of a different type so as to allow radiological acquisitions and therefore radiological images with different parameters and/or of a different type (for example magnetic). Additional source 27 is configured to emit an additional acquisition beam configured to traverse a portion of the patient to be analyzed and then be acquired by an additional detector of said additional beam.

Additional source 27 may comprise an additional emission apparatus 271. Additional emission apparatus 271 can comprise an additional body for emitting said additional acquisition beam, an additional collimator of the additional beam and in some cases an additional light source for illuminating scanning zone 2*d* and in particular of the portion to be analyzed.

Additional source 27 may comprise an additional connector 272 for engaging connector 26. Additional emission apparatus 271, when additional source 27 is connected to connector 26, may be close to the front face of gantry 2 and, in particular, enclosing source 21 between additional emission apparatus 271 and the support (in detail, rotor 23).

Additional source 27 may not be supported by gantry 2. It may comprise a support 273 configured to constrain additional source 27 (in detail, additional emission apparatus 271) to an external structure (such as support surface 1*b*, a wall, and/or a ceiling) so as to unload on it the weight of additional source 27.

Additional source 27 can comprise a driver 274 configured to move additional emission apparatus 271 with respect to support 273. Driver 274 can be configured to translate additional emission apparatus 271 with respect to support 273 along a vertical and/or horizontal direction.

Additional source 27 may comprise a connection cable 275 (suitably for data and/or for power) of additional emission apparatus 271 to additional connector 272; and suitably an additional support 276 configured to constrain cable 275 to said external structure. Additional support 276 can define an element distinct from gantry 2 (in detail with respect to the rest of radiological imaging device 1); therefore gantry 2 does not support additional source 27. In fact, additional support 276 can comprise one or more attachments 276*a* configured to fasten solidly (preferably in a resolvable way) cable 275 to said external structure.

It should be noted how the control unit, when additional source 27 is associated with connector 26, prevents the movement of gantry 2 and in particular at least the rotation of rotor 23.

Gantry 2 can comprise a casing 28 defining a housing for the above-described components of gantry 2 except for the possible additional source 27. It should be noted that connector 26 is accessible from the outside of casing 28.

Connector 26 can be configured to bind additional source 27 external to casing 28 and therefore to gantry 2. It therefore defines an attachment for additional source 27 in view from the outside with respect to casing 28.

Gantry 2 can comprise an acquirer 29 configured to perform an optical acquisition. Acquirer 29 can be integral with rotor 23. Acquirer 29 is configured to perform an optical acquisition along an axis substantially parallel to the positioning plane of acquisition axis 2*a* in detail substantially parallel to pointing axis 2*f* and in more detail substantially coinciding with pointing axis 2*f*. It is in data connection with the control unit. Acquirer 29 is configured to perform an optical acquisition of at least part of scanning zone 2*d* and in particular of the portion to be analyzed of a patient and therefore of at least part of scanning zone 2*d*. Acquirer 29 can be configured to perform an optical acquisition of at least optical reference 2*e*. It can be configured to perform an optical acquisition of at least one medical instrument 1*c* so as to allow identification of the instrument and in particular the real position of medical instrument 1c suitably with respect to scanning zone 2d and in particular to the portion to be analyzed and for the precision to optical reference 2e.

In particular, radiological imaging device 1 and, to be more precise, the control unit can define the real position of medical instrument 1c based on at least the acquisition of optical reference 2e. The term "position" in this document identifies one or more coordinates aimed at identifying the position of medical instrument 1c with respect to a reference system, for example, the intersection between rotation axis 2c (defining the X axis of said reference system) and resting plane (defining the Y and Z axes identifiable as perpendicular axes defined with respect to each other on the basis of an angular rotor-stator position along said lying plane) of gantry 2 at an end stroke along axis 4a.

Optical reference 2e can identify the origin of a reference system with respect to which to position medical instrument 1c. For example, optical reference 2e can identify a point where the operator places/arranges medical instrument 1c. It can for example identify the insertion point of medical instrument 1c. Therefore, optical reference 2e can identify a point of medical instrument 1c such as functional end 1d of the instrument, that is, from the end of the instrument to be used on the patient such as the cutting profile of a scalpel. In addition, or as an alternative, said real position/orientation of medical instrument 1c can be defined on the basis of at least the acquisition of the same medical instrument 1c. In particular, acquirer 29 is configured to perform an optical acquisition of medical instrument 1c through which the control unit can define the real position of medical instrument 1c.

In some cases, device 1 and in detail the control unit can comprise an instrument database associating to each instrument a profile (suitably three-dimensional) of medical instrument 1c and in particular of functional end 1d so as to allow to verify the correct positioning of medical instrument 1c and therefore of functional end 1d with respect to scanning zone 2d and in particular to the portion to be analyzed and, for accuracy, to optical reference 2e.

Acquirer 29 can be integral with rotor 23. It can therefore be rotated around rotation axis 2c so as to perform an optical acquisition of at least part and in detail of the totality of the portion to be analyzed.

Radiological imaging device 1 can comprise a support structure 3 for supporting gantry 2 and resting, suitably in use, on support surface 1b. In use, support structure 3 is configured to arrange gantry 2 distant from support surface 1b. In detail, support structure 3 can define a vertical distance between gantry 2 and support surface 1b which is practically less than 30 cm, in detail at 20 cm and suitably substantially comprised between 1 cm and 10 cm. Support structure 3 can comprise a first column 31 bound to gantry 2 suitably at a first lateral face of gantry 2 and a second column 32 bound to gantry 2 suitably in correspondence with a second lateral face of gantry 2 suitably opposite the first face with respect to gantry 2.

In detail, first column 31 can be placed on the side opposite to second column 32 with respect to longitudinal axis 1a and/or rotation axis 2c. Columns 31 and 32 are not superimposed on the projection of scanning zone 2d and in detail of gantry 2 along longitudinal axis 1a and/or rotation axis 2c. Gantry 2, as better described below, is therefore free to slide with respect to columns 31 and 32 along longitudinal axis 1a and/or rotation axis 2c without interfering with columns 31 and 32. Gantry 2 has a longitudinal length (or rather along longitudinal axis 1a) almost at least equal and in detail almost superior to that of support structure 3 and therefore of columns 31 and 32.

Radiological imaging device 1 can be mobile and therefore support structure 3 can comprise means for moving radiological imaging device 1 on support surface 1b. The movement means can be in data connection with and therefore can be controlled by the control unit. The movement means can define a movement axis 3a of device 1 substantially perpendicular to longitudinal axis 1a. In detail, they comprise first movement means 33 associated with first column 31 and second movement means 34 associated with second column 32. First movement means 33 can be motorized and in detail comprise at least one driving wheel suitably defining a traction axis substantially parallel to longitudinal axis 1a. Additionally, first movement means 33 can comprise at least one idle rolling element. Second movement means 34 can be idle and in detail comprise at least one idle wheel suitably pivoting.

In order to stabilize radiological imaging device 1 during a radiological acquisition, support structure 3 can comprise at least one stop configured to lock device 1 to support surface 1b. The at least one stop can define, for radiological imaging device 1, a transport configuration wherein the movement means identifies the only contact of device 1 with support surface 1b and a non-transport configuration wherein the movement means does not identify the only contact of device 1 with support surface 1b and in detail are not in contact with support surface 1b. The at least one stop can comprise at least a first stop 35, suitably only one, integral with first column 31 and at least a second stop 36, suitably only one, integral with second column 32. First stop 35 comprises a first plug 351 configured to come into contact with support surface 1b and a first actuator 352 configured to move first plug 351 almost perpendicular to support surface 1b. In the transport configuration, first plug 351 is not in contact with support surface 1b; in the non-transport configuration, first plug 351 is in contact with support surface 1b. First plug 351 can comprise rubber or another high friction contact element with support surface 1b.

A second stop 36 comprises a second plug 361 configured to contact support surface 1b and a second actuator 362 configured to move the first plug almost perpendicular to support surface 1b. In the transport configuration, the second plug 361 is not in contact with support surface 1b; in the non-transport configuration, second plug 361 is in contact with support surface 1b.

Second plug 361 can comprise rubber or another high friction contact element with support surface 1b.

Radiological imaging device 1 can comprise at least one guide 4 defining a translation axis 4a of gantry 2 with respect to support structure 3 suitably substantially parallel to rotation axis 2c. Translation axis 4a can be substantially parallel to longitudinal axis 1a. It can be substantially parallel to support surface 1b. Translation axis 4a can be substantially perpendicular to the scanning axis and in detail to waving axis 2b.

Guide 4 can be external to the vertical projection of scanning zone 2d defining a free access area to scanning zone 2d and therefore through which the patient can position himself in proximity to it, allowing gantry 2 to translate along translation axis 4a by performing a multi-stack radiological acquisition. In particular, it can be external to the vertical projection of gantry 2. Guide 4 can be external to the horizontal projection of the entire gantry 2. The vertical projection is therefore to be identified as the projection on support surface 1b. Therefore, guide 4 can be external to the vertical projection of scanning zone 2d and therefore to the projection on support surface 1b of scanning zone 2d (more simply, the vertical projection can be substantially imagined as the hypothetical shadow, in this case, of scanning zone 2d on the support surface given by a light (in detail, a hypothetical cylindrical light beam) perfectly perpendicular to the support surface).

Gantry 2 has a longitudinal length substantially at least equal to and in detail substantially greater than that of guide 4 and therefore of the stroke of guide 4. The at least one guide 4 can comprise a first guide 4 interposed between first column 31 and gantry 2 and therefore binding said first column 31 to said gantry 2 and a second guide 4 interposed between second column 32 and gantry 2 and therefore binding said second column 32 to said gantry 2. Preferably both guides 4 are motorized. They can be implemented synchronously. The guides 4 can be in data connection with and therefore can be controlled by the control unit. At least one guide 4 can comprise a translation encoder configured to measure the translation along translation axis 4a. Optionally, the control unit, when additional source 27 is associated with connector 26, prevents the movement of gantry 2 along translation axis 4a.

Radiological imaging device 1 can comprise a conduction apparatus 5 configured to control the movement of device 1 along support surface 1b and preferably at least movement means 33 and/or 34. Conduction apparatus 5 can be in data connection with the control unit. It can comprise a shooting block 51 defining a shooting axis 51a which is suitably almost transverse and in detail almost perpendicular to longitudinal axis 1a. Shooting axis 51a can be substantially horizontal. Shooting block 51 can comprise a camera suitably of the optical type. It can be integral with second column 32. Conduction apparatus 5 can comprise control means 52. Control means 52 is configured to control the movement of imaging device 1 on support surface 1b. Preferably the control means allows manual control and therefore can comprise at least one handle. In addition, and/or as an alternative, the control means allows automatic guidance of the device, that is, it can be controlled exclusively by the control unit which can be equipped, for example, with a geo-localization system. Control means 52 can be integral with first column 31. It can be seen how control means 52 can allow the operator to control the operation of the entire radiological imaging device 1 and therefore the execution of a radiological acquisition.

Conduction apparatus 5 may comprise a detecting unit 53 of obstacles like for example a camera. Detecting unit 53 is configured to detect the presence of obstacles during any movement of radiological imaging device 1. In detail, it can detect the presence of obstacles during the movement of device 1 along support surface 1b. It can be integral with first column 31 and/or with second column 32. Alternatively, or in addition, detecting unit 53 can detect the presence of obstacles during the translation of gantry 2 along translation axis 4a. It can be integral with gantry 2. It can comprise a sensor configured to emit a wave (such as ultrasonic and/or electromagnetic) configured to intercept an obstacle. Said sensor can be a known parking sensor.

Conduction apparatus 5 can comprise at least one screen 54 for viewing the filming of shooting block 51 and/or of detecting unit 53. Screen 54 can be integral with first column 31.

Radiological imaging device 1 can comprise a power supply 6 of the entire radiological imaging device 1. In particular, power supply 6 can be connected to connector 26 so as to power the possible additional source 27. Power supply 6 can be integral with gantry 2 or with support structure 3 (in detail first column 31 or second column 32). Preferably it is integral with gantry 2. It can be at least partially and in detail totally constrained to stator 24. Power supply 6 can comprise at least one battery. It may include a connection to an external power supply network.

Radiological imaging device 1 can comprise an interface 7 of data exchange between the operator and the control unit (and therefore the various components of the device). Interface 7 can be integral with gantry 2 and in detail with stator 24. Interface 7 can be an input and therefore allow the operator to enter data such as, for example, the command data of device 1. In addition, or alternatively, interface 7 can be an output and therefore can allow device 1 to communicate data to the operator, such as, for example, the result of a radiological acquisition, that is, a radiological image.

It should be noted that radiological imaging device 1 may have no patient support structure (such as a radiological bed) which, in any case, can be used in combination with device 1 during a radiological acquisition. It is therefore structurally separated from the patient support structure and therefore movable (integrally or only gantry 2) with respect to the patient support structure.

In some cases, radiological imaging device 1 and in detail the control unit can comprise an acquisitions database associated with each radiological acquisition and the point/angle (or rather the coordinates), wherein said radiological acquisition was performed. In particular, the acquisitions database associates each point of the radiological image (suitably constructed on the basis of one or more acquisitions) with at least one virtual coordinate identifying the position of said point in the image, or rather with respect to scanning zone 2d and in particular to the portion to be analyzed. Said at least one virtual coordinate can comprise the angular position (or rather the angle) of rotor 23 with respect to stator 24. Finally, device 1 can comprise one or more medical instruments.

It should be noted that radiological imaging device 1 can comprise for one or more and preferably the totality of the movements (rotations and/or translations) performed/implemented by it, encoders or other measuring means of said movement so as to allow each point of the radiological image to associate with a point in space relative to the same device. Device 1 and in detail the control unit are configured to associate, conveniently due to the acquisition database and/or said measurement means, each virtual coordinate of a point in the radiological image with a real coordinate (with respect to an absolute reference and/or of the device) to identify the position of the point with respect to the device.

Figure 6:
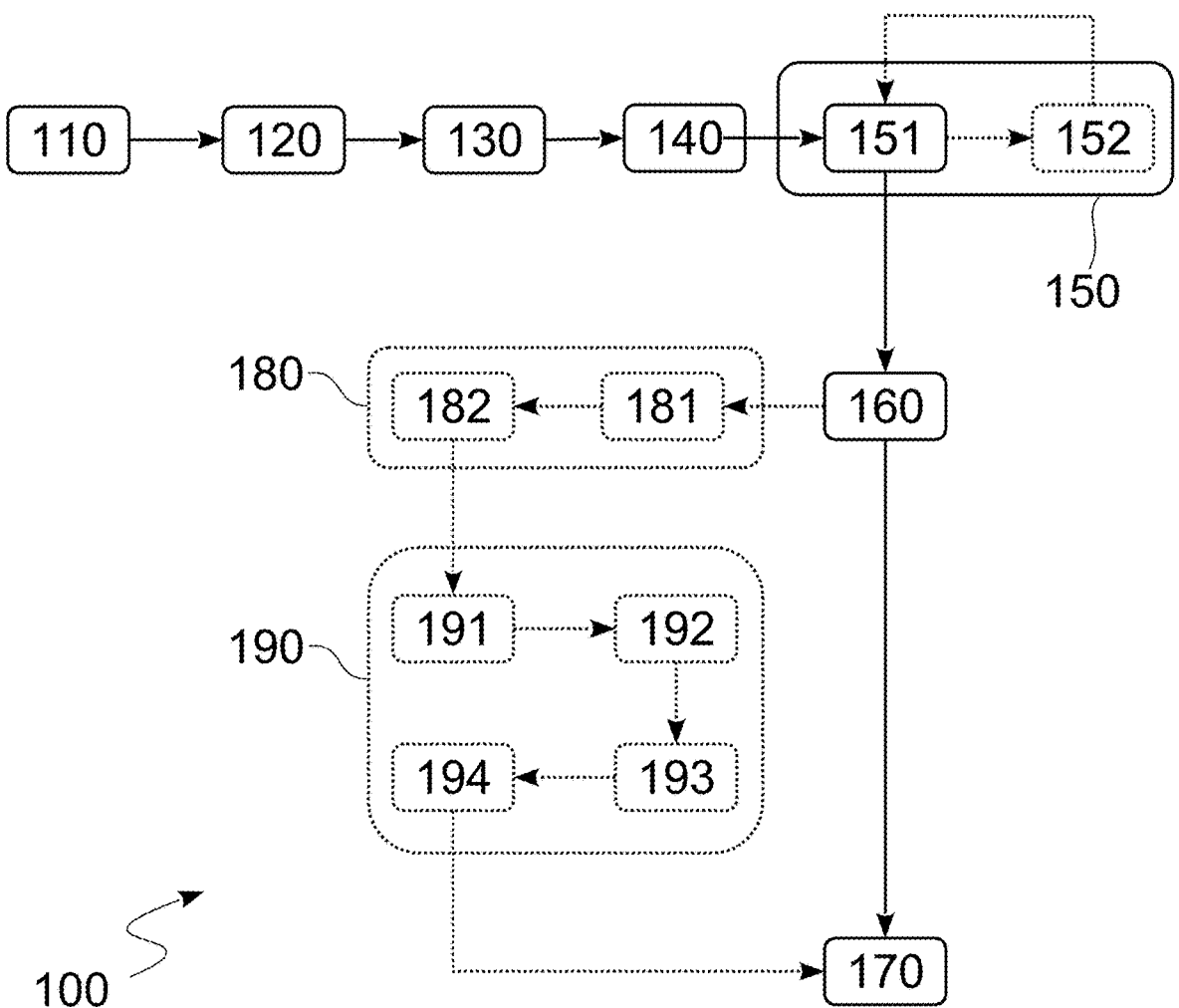
FIG. 6 is a schematic of the operation of the radiological imaging device according to the invention.
Figure 7:
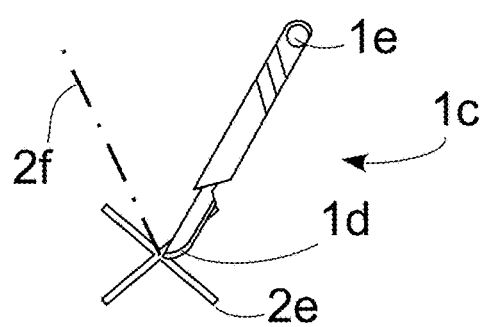
FIG. 7 shows a medical instrument that may be used within the imaging device according to the invention.

The operation of radiological imaging device 1 previously described in structural terms is as follows. This operation defines a new acquisition procedure 100 by which radiological imaging can be implemented by radiological imaging device 1 and described below. Radiological imaging acquisition procedure 100 is controllable and therefore executable by the control unit preferably automatically and/or in response to at least one command given by the operator. Acquisition procedure 100 is represented in FIG. 6. Acquisition procedure 100 can be implemented once the portion to be analyzed or at least part of it is in scanning zone 2d.

Acquisition procedure 100 may comprise a placement phase 110 for placing device 1. In phase 110, radiological imaging device 1, with stops 35 and 36 in the transport configuration, is operated in correspondence with the environment, where the acquisition occurs due to driving means 33 and 34 and conduction apparatus 5. This operation can be performed automatically (therefore controlled by the control unit) and/or manually (therefore controlled by the operator).

Once the desired position has been reached, placement phase 110 is concluded by bringing radiological imaging device 1 into the non-transport configuration, or rather stops 35 and 36 in contact, preferably exclusively, with support surface 1b.

Acquisition procedure 100 can comprise a selection phase 120 of the radiological acquisition parameters. Said phase can be controlled by the operator through said interface.

Acquisition procedure 100 can comprise a centering phase 130 of device 1 with respect to scanning zone 2d and in particular to the portion to be analyzed. This operation can be performed using, for example, at least one of the pointing apparatus of source 21, projector 222 of detector 22 and radiological acquisitions, for example, lateral, suitably of the fluoroscopy type. In some cases, centering phase 130 can be performed by exploiting optical reference 2e with respect to scanning zone 2d and in particular to the portion to be analyzed. In this case source 21, detector 22 and optical pointer 25 are moved (suitably translated along translation axis 4a and/or rotated around translation axis 4a and/or they can be rotated with respect to rotation axis 2c) so as to place optical reference 2e in correspondence with scanning zone 2d in particular of the portion to be analysed. In this case, acquisition procedure 100 can comprise a rotation phase 140 wherein rotor 23 rotates by an angle equal to the angle of spread between acquisition axis 2a and pointing axis 2f, arranging acquisition axis 2a substantially parallel to pointing axis 2f in centering phase 130. In detail, at the end of phase 140, acquisition axis 2a is substantially in the position of pointing axis 2f at the end of centering phase 130.

After centering, acquisition procedure 100 may comprise an acquisition phase 150 of at least a radiological image. Acquisition phase 150 can comprise at least one scanning sub-phase 151 in which source 21 emits an acquisition beam which crosses the portion to be analysed and is therefore detected by detector 22 obtaining a radiological acquisition. In acquisition sub-phase 151, rotor 23 can rotate around scanning zone 2d suitably by an acquisition angle so as to simultaneously move source 21 and detector 22 around the portion to be analysed. Conveniently, in each acquisition sub-phase 151, the above-mentioned database of acquisitions can be defined associating each acquisition with the point/angle wherein said radiological acquisition was performed. The number of scanning sub-phases 151, or rather of radiological acquisitions, identifies the stack number. It is proportional to the ratio between the scanning length (or rather, the length of the portion to be analysed along translation axis 4a) and the active length (or rather the length of the sensitive surface of detector 22 along translation axis 4a) suitably rounded up. The active length can be stored on the control unit. The acquisition length can be defined by the operator through this interface.

In detail, acquisition phase 150 can comprise only one scanning sub-phase 151 if the active length is substantially not greater and in detail substantially less than the acquisition length. In this case, device 1 performs a single stack acquisition. Alternatively, acquisition phase 150 can comprise a plurality of scanning sub-phases 151 if the active length is substantially greater than the acquisition length. In this case, device 1 performs a multi-stack radiological acquisition. In this case phase 150 can suitably comprise at least one translation sub-phase 152 wherein the at least one guide 4 translates gantry 2 along translation axis 4a. This translation of gantry 2 can be almost less than the active length. Each translation sub-phase 152 is interposed between two consecutive scanning sub-phases 151. It is noted that in acquisition phase 150 and in detail in each scanning sub-phase 151, an optical acquisition of at least part and in detail of the totality of the portion to be analysed can be performed. In particular, acquirer 29 can rotate around rotation axis 2c by carrying out said optical acquisition.

At the conclusion of the acquisition phase 150, acquisition procedure 100 can comprise a reconstruction phase 160, wherein the radiological image is reconstructed on the basis of one or more radiological acquisitions performed in acquisition phase 150; and suitably a video displaying phase 170 for said radiological image via said interface. Said phases 160 and 170 are known per se.

Acquisition procedure 100 can comprise a planning phase 180 in which an ideal position of a medical instrument 1c is suitably defined with respect to scanning zone 2d and in particular to the portion to be analysed and wherein optical pointer 25 and therefore reference 2e are moved according to said ideal position. The ideal position of medical instrument 1c identifies the point and preferably the orientation that medical instrument 1c should ideally assume with respect to the radiological image (therefore to the patient) before starting the intervention. It can thus only identify the position of medical instrument 1c with respect to the patient but not how to insert it into the patient and/or perform the operation itself. The ideal location includes a set of coordinates. In detail, it comprises a first set of coordinates (hereinafter referred to as "the ideal target") defining the point in the radiological image where medical instrument 1c and in particular functional end 1d is to be placed; and a second set of coordinates (hereinafter referred to as "the ideal inclination") defining the inclination/orientation of medical instrument 1c when it has functional end 1d in the ideal target. The ideal target is substantially external to the patient and in detail on the skin or other visible surface of the patient, or rather on the perimeter sector. Planning phase 180 can be subsequent to reconstruction phase 160 and in detail of video displaying phase 170. It can be prior to and/or contemporaneous with video displaying phase 170. The ideal position identifies the position in which instrument 1c must be to start and then perform an operation correctly. Planning phase 180 defines the ideal contact position of a medical instrument 1c with the patient before performing the operation.

Planning phase 180 may comprise a selection sub-phase 181, wherein the ideal position of medical instrument 1c is defined by identifying at least an ideal target and an ideal inclination on the radiological image and a pointing sub-phase 182 of optical pointer 25 and therefore of optical reference 2e. The radiological image can therefore comprise and in detail define an intervention target and an intervention trajectory preferably in addition to a graphic reproduction of at least the sector of interest. Therefore, in selection sub-phase 181 an intervention target and an intervention trajectory can be selected on the radiological image. This selection can be automatic, or rather performed only by the control unit, for example following an input given by the operator, or manual, or rather by the operator selecting the intervention target and insertion trajectory on the radiological image. The intervention objective identifies a point on the radiological image, while the intervention trajectory identifies a direction along which to move/insert and then position medical instrument 1c. At this point the ideal position of medical instrument 1c is suitably defined as a function of objective and trajectory of intervention by the control unit alone.

The ideal target depends on the intervention objective and in some cases the intervention trajectory. In detail, if the intervention objective is a point in the perimeter sector of the radiological image (for example a point on the patient's skin), the intervention objective is the ideal target. Alternatively, if the target is a point in the sector of interest of the radiological image (therefore being a point inside the patient such as an organ or a bone), the ideal target is identified as the intersection between the perimeter sector and the trajectory of the intervention.

The ideal inclination can be a function of the intervention trajectory. In particular, it is substantially parallel and preferably almost coincident with the insertion trajectory.

Once the ideal position has been identified, pointing sub-phase 182 occurs in which gantry 2 can move optical pointer 25 by arranging pointing axis 2f incident to the ideal target and therefore optical reference 2e in correspondence with the ideal target. In pointing sub-phase 182, optical pointer 25 is moved by rotating rotor 23 around rotation axis 2c and/or by translating gantry 2 along translation axis 4a so as to have optical reference 2e in correspondence with the target ideal of selection sub-phase 181. It is noted how this operation, as well as others even if not specified, is possible due to the association of each virtual coordinate of a point in the radiological image to a real coordinate and therefore to virtual coordinates of the ideal target to the real coordinates of the same ideal target and of the virtual coordinates of the ideal inclination to the real coordinates of the same ideal inclination.

Acquisition procedure 100 can comprise an orientation phase 190 of a medical instrument 1c with respect to scanning zone 2d and in particular to the portion to be analysed. Orientation phase 190 can be subsequent to planning phase 180 and in detail to pointing sub-phase 182. It can be prior to and/or contemporaneous with video displaying phase 170. In orientation phase 190, the control unit compares the real position of medical instrument 1c, or rather the position according to an optical acquisition, with respect to the ideal position and in detail to the ideal target and the ideal inclination.

Orientation phase 190 can comprise a positioning sub-phase 191 of medical instrument 1c in scanning zone 2d (in particular in contact with the portion to be analysed) suitably in correspondence with the optical reference 2e preferably with the proximal functional end 1d and in detail in contact with optical reference 2e. In positioning sub-phase 191 and therefore in orientation phase 190, only the positioning of medical instrument 1c can be provided. The insertion of medical instrument 1c and/or the execution of the intervention can thus be excluded from them.

Orientation phase 190 can comprise a shooting sub-phase 192 wherein an optical acquisition of the position of the instrument 1c and suitably of optical reference 2e is performed. In shooting sub-phase 192, acquirer 29 takes up medical instrument 1c (in detail at least functional end 1d) and suitably optical reference 2e. Shooting sub-phase 192 can be performed when, due to the optical acquisition, functional end 1d is identified in correspondence with optical reference 2e.

Orientation phase 190 can comprise a verification sub-phase 193 wherein a real position of medical instrument 1c is defined and then checked whether it is in the ideal position with respect to scanning zone 2d and in particular to the portion to be analysed and/or to optical reference 2e. In verification sub-phase 193, a real position of medical instrument 1c is defined as a function of said optical acquisition performed in sub-phase 192 (suitably to the tools database) and therefore the real position is compared with the ideal position and therefore with an ideal inclination and ideal target. The real position can be a function of said optical acquisition of medical instrument 1c and suitably of optical reference 2e and in some cases of the instruments database. In this sub-phase 193, the control unit identifies, with respect to scanning zone 2d and in particular and to the portion to be analysed (in detail at optical reference 2e), the real position by defining the real target and preferably the real inclination suitably with respect to an absolute and/or specific reference of the device. The real target identifies the point where medical instrument 1c actually is (in particular functional end 1d) with respect to scanning zone 2d and in particular to the portion to be analysed.

Orientation phase 190 may comprise a signalling sub-phase 194, for example through interface 7, whether medical instrument 1c is substantially or not in said ideal position. In detail, the control unit compares the real position with the ideal one. If the difference between these positions is substantially lower than an acceptability threshold in signalling sub-phase 194, the control unit signals the correctness of the position of medical instrument 1c.

It is pointed out that, as anticipated above, phases 190, 180, and/or 170 (and in detail 150 and 160) can be performed simultaneously so as to allow the operator to follow the movement of medical instrument 1c.

Radiological imaging device 1 and procedure 100 according to the invention achieve important advantages. In fact, radiological imaging device 1 and procedure 100, due to the use and in particular to the particular positioning of optical pointer 25, produce a particularly rapid and precise targeting. Another important advantage is represented by the fact that radiological imaging device 1 and procedure 100 allow the execution of a wide typology of radiological acquisitions due above all to the presence of connector 26 which allows the use of an additional source 27. Another advantage is that radiological imaging device 1, compared to known radiological imaging devices, has a relatively simple structure and therefore has a low purchase and maintenance cost and is easy to manufacture and use.

Another advantage is provided by guides 4 and in detail by the particular structure 3 which allows gantry 2 to translate and therefore to perform a multi-stack radiological acquisition without interfering with the operator. In fact, since guide 4 is external to the vertical projection of scanning zone 2d and in particular of the gantry, it defines a free access area through which the patient can easily position himself near scanning zone 2d and allows the gantry to be moved along translation axis 4a without interfering with the patient himself and/or components of device 1. The access area substantially identifies a free space (i.e., not occupied by device 1) in which the patient (appropriately supported by a bed or other radiological support) can be arranged during a radiological acquisition. The access area can for example be the space defined by the horizontal projection of gantry 2 due to the position of columns 31 and 32 with respect to gantry 2 itself.

In this document a "projection" identifies an orthogonal projection and then a space/area delimited by the projection of a point/area/volume along lines perpendicular to a given plane. Therefore, the vertical projection for example of scanning zone 2d identifies the space enclosed by the projection of scanning zone 2d along lines substantially perpendicular to support surface 1b when device 1 is resting on it. In the same way, the horizontal projection for example of gantry 2 identifies the space enclosed by the projection of scanning zone 2d and preferably gantry 2 along lines substantially parallel to support surface 1b when device 1 rests on it.

Furthermore, the use of the particular guides 4 and of a support structure able to distance gantry 2 from support surface 1b allows, for example, to place a radiological bed or other radiological support extremely close to device 1. In particular, said spacing between support surface 1b and gantry 2 allows any support of the radiological support to be inserted between support surface 1b and gantry 2 allowing a practical juxtaposition of the patient placed in scanning zone 2d and in detail on said support surface of the radiologic support.

The invention is susceptible of variants falling within the scope of the inventive concept defined by the claims. For example, detecting unit 53 may comprise a hinge configured to allow the camera itself to rotate with respect to device 1 (in detail second column 32) by varying the inclination of shooting axis 53a with respect to longitudinal axis 1a and/or to support surface 1b. Said hinge can be motorized. This inclination variation can be controlled automatically (or rather from the control unit) and/or manually by the operator, for example through the interface.

In another example additional emission apparatus 271, when additional source 27 is connected to connector 26, can be arranged in proximity to the rear face of gantry 2 and therefore on the opposite side to source 21 with respect to the gantry itself.

In another example, in reconstruction phase 160, the optical image can be reconstructed on the basis of the one or more optical acquisitions performed in acquisition phase 150. Preferably in reconstruction phase 160 a composite image of the optical image and the radiological image can be reconstructed. The composite image can be identified by an image, for example three-dimensional, wherein the optical image represents the external profile and the radiological image identifies the internal structure. The operator can then decide whether to view the external profile to identify an area of interest (easily identifiable on the patient) and then view the underlying internal structure called an area of interest.

It should be noted that in video displaying phase 170, medical instrument 1c and suitably the optical and/or composite image can be exposed. The association between optical image and radiological image can be performed by exploiting, for example, the acquisitions database and in particular the association between each single radiological acquisition and the point/corner where said radiological acquisition was performed. The optical image and in particular the composite image can be used in planning phase 180. In this case in planning phase 180, the operator can select the target on the external profile.

In some cases, medical instrument 1c, to perform the identification of its position and/or orientation, can comprise one or more additional optical references 1e (for example a colored block) which can be acquired by acquirer 29. Preferably one or more additional optical references 1e are available in a distal position from each other and in particular from optical reference 2e (in detail from functional end 1d of the instrument). In this case in orientation phase 190 (in detail in shooting sub-phase 192), acquirer 29 also acquires one or more additional optical references 1e. Therefore, in verification sub-phase 193, the real position of medical instrument 1c with respect to scanning zone 2d is also determined as a function of one or more additional optical references 1e.

It should be noted that one or more of the aforementioned examples can be simultaneously provided in radiological imaging device 1 and/or integrated with any of the characteristics of device 1 described above. In this context, all the details can be replaced by equivalent elements and the materials, shapes and dimensions can be any.

The invention claimed is:

1. A radiological imaging device configured to acquire a radiological image comprising a sector of interest representative of said portion to be analyzed of the patient and a perimeter sector of said sector of interest, said radiological imaging device comprising:
    a gantry configured to perform the radiological acquisition of at least a portion of the patient to be analyzed, the gantry comprising:
        a source configured to define an acquisition beam and an acquisition axis;
        a detector configured to obtain at least one radiological acquisition when said acquisition beam is incident thereupon after said acquisition beam has passed through said portion to be analyzed;
        a rotor supporting at least said source and said detector; and
        a stator supporting said rotor and configured to rotate said rotor to define a rotation axis; and
    a control unit for the operation of said radiological imaging device, the control unit configured to define said at least one radiological image as a function of said at least one radiological acquisition,
    wherein said gantry further comprises:
    an optical pointer integral with said rotor and configured to project an optical reference along a pointing axis; and
    an acquirer integral with said rotor and configured to perform an optical acquisition of at least said optical reference and of a medical instrument placed in correspondence with said optical reference; and
    wherein an intervention target and an intervention trajectory are identified in said radiological image, and said command unit:
    defines for said medical instrument an ideal inclination according to at least said intervention trajectory and, on said perimeter sector, an ideal target according to at least said intervention objective, said ideal inclination and said ideal target, defining an ideal position of this medical instrument,
    commands said optical pointer, by rotating said rotor around said rotation axis, to place said optical reference in correspondence with said ideal target and to said acquirer to perform an acquisition of said medical instrument placed in correspondence with said optical reference defining a real position of said medical instrument; and
    compares said real position of said medical instrument in said optical acquisition with respect to said ideal position.

2. An acquisition method using a radiological imaging device configured to acquire a radiological image comprising a sector of interest representative of a portion to be analyzed of the patient and a perimeter sector of said sector of interest,; said radiological imaging device comprising:
    a gantry configured to perform the radiological acquisition of at least a portion of the patient to be analyzed, the gantry comprising:
        a source configured to define an acquisition beam and an acquisition axis; and
        a detector configured to have said acquisition beam incident
    thereupon after said acquisition beam has passed through said portion to be analyzed, wherein said gantry further comprises:

an optical pointer integral with said rotor configured to project an optical reference along a pointing axis inclined with respect to said acquisition axis by a spreading angle; and an acquirer configured to perform an optical acquisition of at least said optical reference and of a medical instrument placed in correspondence with said optical reference; and wherein said acquisition method includes:
   an acquisition phase of at least a radiological image of said portion to be analyzed;
   a selection sub-phase wherein:
      in said radiological image an intervention target and an intervention trajectory are identified and said command unit; and
      an ideal inclination according to at least said intervention trajectory and, on said perimeter sector, an ideal target according to at least said intervention objective are defined for said medical instrument, said ideal inclination and said ideal target defining an ideal position of said medical instrument;
   a pointing sub-phase wherein by rotating said rotor around said rotation axis said optical pointer is moved by arranging said pointing axis incident said ideal target and said reference optical in correspondence with said ideal target;
   a shooting sub-phase wherein an optical acquisition is performed of said medical instrument placed in correspondence with said optical reference; and
   a verification sub-phase wherein a real position of said medical instrument is defined as a function of said optical acquisition and said real position of said medical instrument is compared with said ideal position of said medical instrument.

3. The acquisition method according to claim 2, comprising an instrument database associating with each of said medical instrument a profile of said medical instrument,
   wherein, in said shooting sub-phase, said real position of said medical instrument is defined as a function of said profile of said medical instrument.

4. The acquisition method according to claim 3, wherein said medical instrument comprises at least one additional optical reference that can be acquired from said acquirer,
   wherein:
      said optical acquisition of said additional optical reference is performed in said shooting sub-phase; and
      in said verification sub-phase said real position of said medical instrument is defined as a function of said additional optical reference.

* * * * *